United States Patent [19]

McMillan

[11] Patent Number: 4,522,064
[45] Date of Patent: Jun. 11, 1985

[54] ULTRASONIC METHOD AND APPARATUS FOR DETERMINING THE DEPTH OF A CRACK IN A SOLID MATERIAL

[75] Inventor: John D. McMillan, Kennewick, Wash.

[73] Assignee: Sigma Research Inc., Richland, Wash.

[21] Appl. No.: 560,752

[22] Filed: Dec. 12, 1983

[51] Int. Cl.³ .............................................. G01N 29/04
[52] U.S. Cl. ........................................ 73/592; 73/600; 73/628; 73/640
[58] Field of Search ................ 73/592, 599, 600, 627, 73/628, 640, 638, 637

[56] References Cited

U.S. PATENT DOCUMENTS

| 2,660,054 | 11/1953 | Pringle, Jr. ................ 73/627 |
| 2,799,157 | 7/1957 | Pohlman . | |
| 2,937,522 | 5/1960 | McGaughey . | |
| 3,585,851 | 6/1971 | Walther . | |
| 3,683,680 | 8/1972 | Johnson et al. .......... 73/628 |
| 4,270,389 | 6/1981 | Shiraiwa et al. . | |
| 4,393,711 | 7/1983 | Lapides ................... 73/592 |
| 4,435,984 | 3/1984 | Gruber .................... 73/628 |

FOREIGN PATENT DOCUMENTS

| 2740106 | 3/1979 | Fed. Rep. of Germany ........ 73/628 |
| 55-39007 | 3/1980 | Japan ................................... 73/628 |
| 523346 | 11/1976 | U.S.S.R. ............................... 73/628 |

OTHER PUBLICATIONS

"Height Determination Studies for Planar Defects by Means of Ultrasonic Testing"–The Non Destructive Testing Journal, Japan vol. 1, No. 1, 1983.

Primary Examiner—Howard A. Birmiel
Attorney, Agent, or Firm—Wells, St. John & Roberts

[57] ABSTRACT

An ultrasonic method and apparatus are described for determining the depth of cracks 12 in a pipe or conduit 14. The apparatus 10 includes a transmitting transducer 30 and a receiving transducer 40 that are placed on the outside surface of the pipe to one side of the pipe. The transmit transducer 30 is energized to direct a shear wave beam 34 of ultrasonic energy at the crack to generate a complex reflected wave front from the crack 12 which contains information as to the size of the crack in relation to the wall thickness. The recovery transducer 40 is moved relative to the transmit transducer until a peak or maximum amplitude reading is found. When the maximum amplitude is found, the distance between the transducers is measured. The measured distance is then correlated with information obtained from specimens 80 of the same material and wall thickness as the on-site pipe to determine the depth of the crack 12.

9 Claims, 7 Drawing Figures

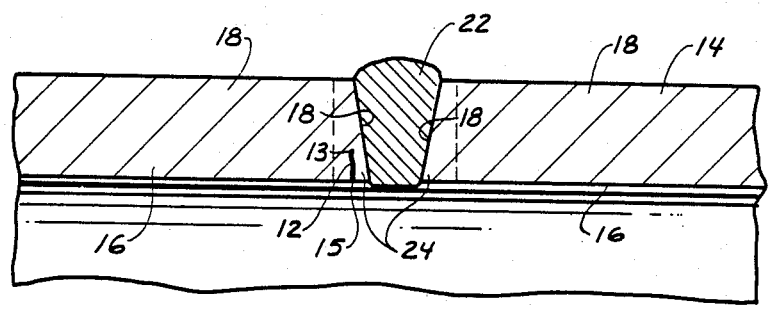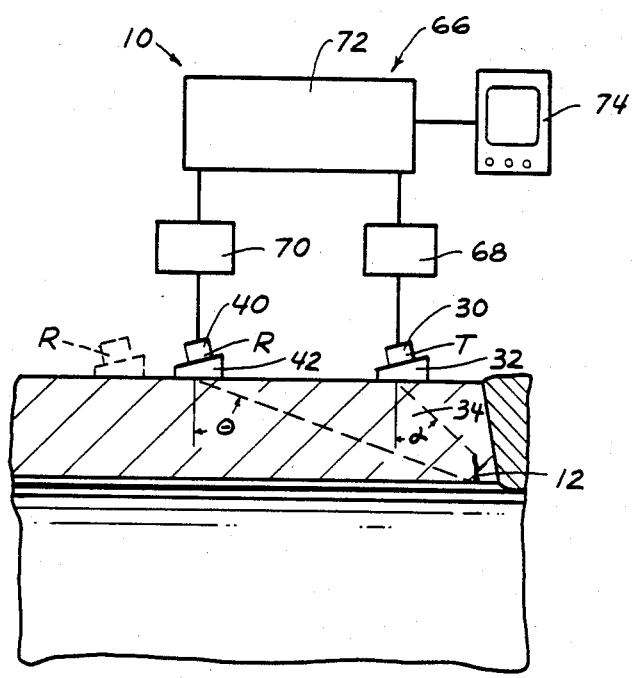

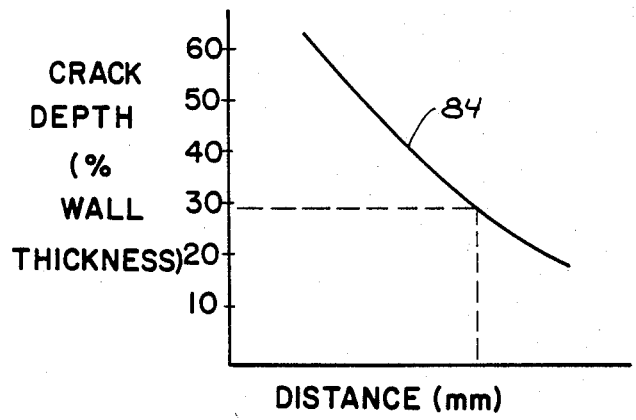
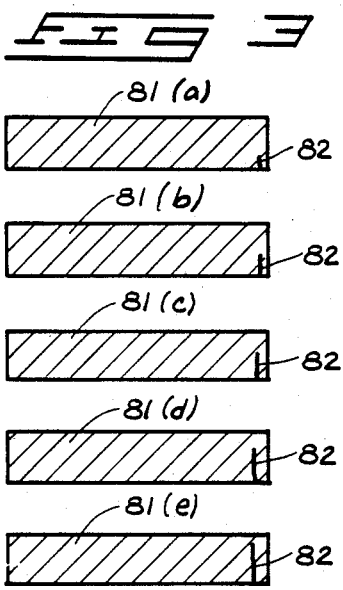
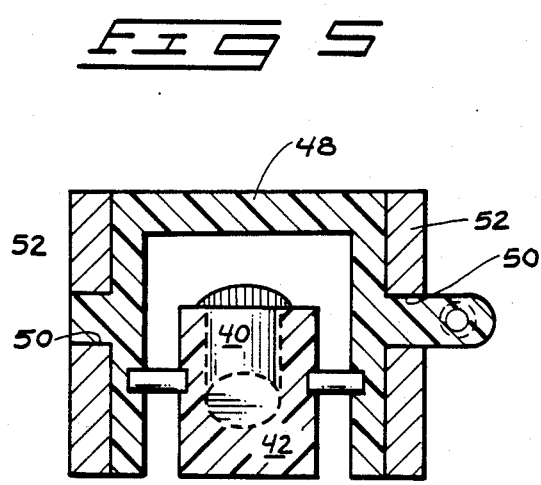

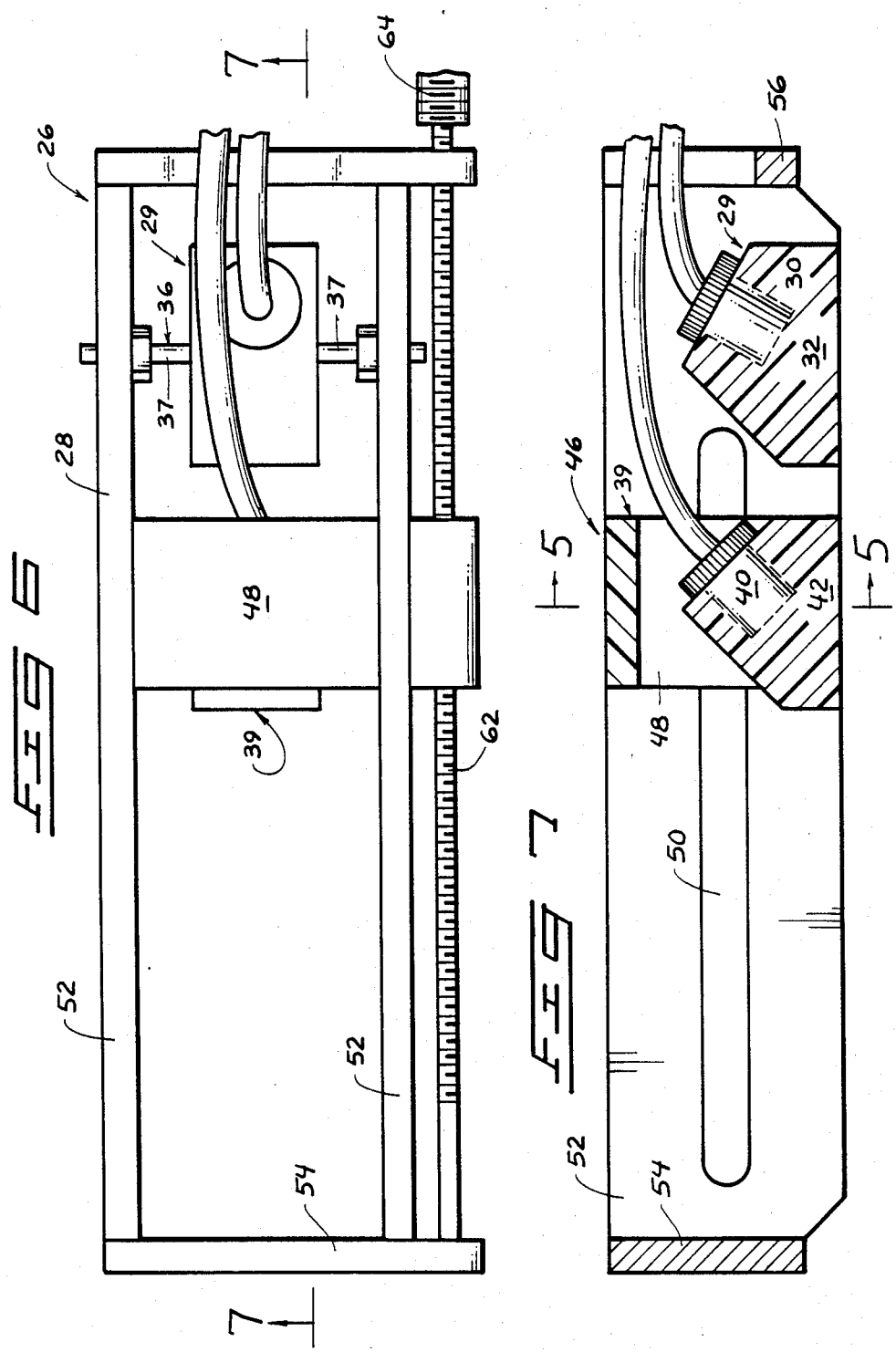

ULTRASONIC METHOD AND APPARATUS FOR DETERMINING THE DEPTH OF A CRACK IN A SOLID MATERIAL

FIELD OF THE INVENTION

This invention relates to ultrasonic, non-destructive testing techniques for determining the depth of discontinuities or cracks in solid material. More specifically, the invention relates to apparatus and methods for detecting the depth of intergranular stress corrosion cracks in stainless steel pipe systems containing fluids.

BACKGROUND OF THE INVENTION

Cracks and particular intergranular stress corrosion cracking is a major problem in stainless steel piping systems carrying hazardous fluids particularly systems containing boiling water for nuclear reactor plants. The intergranular stress corrosion cracking most frequently occurs in regions adjacent to weld areas in the pipe section in which the welding of the pipe joints engenders thermostress in the piping and adjacent the weld. The intergranular stress corrosion is generally thought to originate on the interior walls of the pipe near the weldment and then grow both radially and circumferentially into the pipe section due to the combined affects of stress, heat, and corrosion from the boiling water passing through the pipe. The intergranular stress corrosion cracks are generally referred to as "tight" cracks which visually appear as fissures or veins extending throughout a volume of the pipe.

Not only are the "tight" cracks difficult to detect but it is even more difficult to determine the size or depth of the crack into the pipe section.

With respect to nuclear power plants, a conservative replacement approach is usually taken because of the risks involved in leakage from the power plant piping system. Large stainless steel pipe sections that are welded together are generally used as principal conduits for the primary reactor coolant system. If a crack is detected, the conservative replacement criteria may mandate unplanned shut-down of the reactor. An unplanned down time of approximately a week or ten days to replace a suspected pipe section and restart the reactor is not unusual. Sometimes it is found after the fact that the detected crack was not "critical" and that the power plant could have continued operating safely until the next "scheduled" maintenance shut-down.

The problem and a proposed solution is described in the Melvin E. Lapides U.S. Pat. No. 4,393,711 granted July 19, 1983.

Accordingly, it is the principal object of this invention to provide a unique system for determining the depth or the extent of a detected crack particularly in pipe sections so that one can evaluate the seriousness of the problem. These and other objects, features and advantages of this invention will become apparent upon consideration of the following detailed description taken in conjunction with the accompanying drawings.

BRIEF DESCRIPTION OF THE DRAWINGS

A preferred and alternate embodiment of this invention is illustrated in the accompanying drawings, in which:

FIG. 1 is a longitudinal cross-sectional view of a wall section of a stainless steel pipe conduit illustrating a butt weldment between two pipe sections in which a crack is illustrated opening into the inner surface of the pipe section on one side of the weldment;

FIG. 2 is a schematic block diagram of an ultrasonic apparatus for determining the unknown depth of a crack in the pipe section adjacent to the weldment;

FIG. 3 illustrates a series of cross-sections of a series of calibration specimens of the same material and wall thickness as the pipe section under inspection in which the specimens have cracks of known depths formed therein for calibration purposes;

FIG. 4 is a graph illustrating the correlation between the crack depth and the distance between the ultrasonic transducers illustrated in FIG. 2. The crack depth is presented as a percentage of the depth with respect to the wall thickness. The distance between the transducers is illustrated in millimeters;

FIG. 5 is a cross-sectional view of a section taken along line 5-6 in FIG. 6.

FIG. 6 is a plan view of a transducer frame assembly for receiving and mounting the transducers for mounting the transducers on the pipe sections and for enabling at least one of the transducers to move relative to the other;

FIG. 7 is a cross-sectional side view taken along line 7—7 in FIG. 5.

DETAILED DESCRIPTION OF A PREFERRED EMBODIMENT

In compliance with the constitutional purpose of the Patent Laws "to promote the progress of science and useful arts" (Article 1, Section 8), applicant submits the following disclosure of the invention.

The invention is directed to a nondestructive method and apparatus of determining the height of cracks or discontinuities in solid materials using ultrasonic testing equipment.

FIG. 2 illustrates a preferred embodiment of ultrasonic inspection apparatus, gnerally designated with numeral 10. The apparatus 10 is designed to determine the depth of a crack 12 in a solid material 14. The apparatus 10 is particularly useful in determining the depth of cracks 12 in installed pipe such as stainless steel piping or conduit used in chemical or processing plants or power plants utilizing hazardous fluids. As previously mentioned the apparatus 10 is designed to determine the depth of intergranular stress corrosion cracks 12 (tight cracks) that are normally found adjacent weldments. An installed pipe section is illustrated in FIG. 1 having an inside pipe surface 16 and an outside pipe surface 18. The pipe sections are secured end to end by a circumferential butt weld 22. The weld 22 interconnects beveled end surfaces 18. During welding, heat is transferred into the pipe ends providing heat stress zones, designated by the numeral 24. Intergranular stress corrosion cracks appear in the heat effected zones 24 and migrate from a crack opening 15 on the inside surface 16 into the interior of the pipe wall to a crack tip 13.

The apparatus 10 includes an ultrasonic transducer assembly 26, FIGS. 5, 6 and 7, that has a portable frame 28. Mounted on the frame 28 is ultrasonic transmitting transducer assembly 29 and ultrasonic receiving transducer assembly 39. Assembly 29 includes an ultrasonic transducer 30 with a coupling means 32 for acoustically coupling the transducer 30 to the outside surface 18. The coupling means 32 may be of a liquid material, or a low impedence plastic block that supports, houses and orients the transducer 30 at an inclined angle α with respect to a normal to the surface 18. In a preferred embodiment the transducer 30 is oriented an angle α sufficient to generate predominately shear waves or beams 34 (FIG. 2) to illuminate the crack region. In response to the transmitted ultrasonic wave energy a portion of the wave energy is reflected from the crack 12 and contains information as to the nature and size of the crack 12 for a particular material and wall thickness.

The ultrasonic receiving transducer 39 includes an ultrasonic transducer 40 with a coupling means 42 for acoustically coupling the transducer 40 to the outside surface 18. Preferably the transducer 40 is inclined, facing the crack at an optimum angle θ to receive the reflected ultrasonic energy. Experiments have shown that an angle θ that corresponds to a solid material refraction angle of approximately 60° to the normal is satisfactory.

The transducer assembly 29 includes a mounting means 36 for supporting the transducer 30 to the frame 28. Preferably the transducer 30 and coupling means 32 are supported to the frame 28 in a manner to enable the coupling means 32 to be self-centering to provide good contact between the coupling means 32 and the outside surface 18. As shown in FIG. 6 the coupling means 32 is supported to the frame 28 by stub shafts 37 which enable the coupling means 32 and transducer to pivot about the shafts 37 to obtain maximum contact with and adjust to the contour of the outside surface 18.

The transducer assembly 39 includes a mounting means 46 for supporting the coupling means 42 and the ultrasonic transducer 40 on the frame 28. Preferably the mounting means 46 includes a carriage 48 supporting the transducer 40 that is movable to and from the assembly 29. The carriage 48 has projections that extend into and slide in slots 50 formed in side rails 52. The side rails 52 are interconnected at their ends by cross frame elements 54 and 56.

The carriage 48 may be moved by hand to adjust or change the spacing or distance (D) between the transducers 30 and 40. Preferably, the apparatus 20 has a carriage drive means in the form of a lead screw 62 that is rotated to move the carriage to and fro with precision. In such an arrangement, a micrometer 64 is affixed to the lead screw to enable the screw 62 to be manually or automatically rotated with the spacing (D) accurately measured by the micrometer reading. Various other types of drive mechanisms may be used to accurately move the carriage and measure the spacing (D) between the transducers 30 and 40.

The apparatus further includes an ultrasonic electrical system, generally designated with the numeral 66 (FIG. 2). The system 66 includes an electrical pulse interface 68 connected to the transmitting transducer 30 for generating pulse bursts of ultrasonic energy at desired intervals. The system 66 also includes a receive signal interface 70 for receiving the electrical signal from the receiving transducer 40 and transferring the signal to an electrical signal processing unit 72. The electrical signal processing unit 72 processes the signal for visual display on display unit 74 such as an oscilliscope. From the oscilliscope, the operator is able to determine when the signal reaches a maximum. Alternatively analog-to-digital (A/D) electronic circuitry may be used to analyze the signal and automatically determine when the signal reaches a maximum value.

The method involves placing the transmitting transducer assembly 29 and the receiving transducer assembly 39 on the outside surface 18 of the steel pipe 14 with both assemblies on the same side of the known crack or defect location 12. The transmitting transducer 30 emits the ultrasonic beam 34 illuminating the crack 12. The tip 13 of the crack and the crack opening 15 on the inside surface 16 of the stainless steel pipe 14 act as principal point sources of the reflected wave 44 which is picked up by the receiving transducer 40. The receiving transducer 40 is then moved longitudinally along the outside surface 18 of the steel pipe 14 away from the transmitting transducer 30 until the reflected signal received by the receiving transducer 40 is at a maximum. Since the waves reflected from each point source travel a different distance to the receiving transducer 40 they are out of phase and form interference wave fronts, which affects the amplitude of the total reflected signal received by the receiving transducer 40. When a reflected signal is at a maximum, there is a direct mathematical correlation between the distance between the receiving transducer 40 and the transmitting transducer 30, and the depth of the crack 12. Once the position at which the received signal is at a maximum has been determined, the distance between the two transducers is measured. The distance is then plotted on a calibration curve 84 shown in FIG. 4, and the percent of pipe wall penetration can be obtained.

The calibration curve 84 is constructed applying this method on calibration samples 80 (a–e) of the same material and wall thickness as the pipe 14 being tested. The calibration samples 80 (a–e) contain actual cracks 82 or artificially produced cracks 82 of varying depths. Once the procedure has been accomplished on each known crack 81 in the calibration samples 80, the calibration curve 84 can be constructed. The calibration curve 84 is obtained by plotting the distance between transducers on the X-axis and a percent of pipe wall penetration of the known cracks 81 on the Y-axis.

Once the depth of the crack is known, a determination can be made as to whether replacement of the pipe section can be put off until the next scheduled maintenance, or whether it necessitates shutting down the reactor.

The transducer assemblies can be placed on the material individually, or they may be mounted in the transducer coupling frame means, illustrated in FIG. 5 and FIG. 6. The transducers used in this method range in size from ¼" diameter to 1" diameter with operating frequencies from 0.5 MHz for the larger transducers to 3 MHz for the smaller transducers. The operating frequency depends upon crack depth. The crack depth should exceed the wave length of the illuminating beam 34 by a factor of 4 or 5.

The size of the transmitting transducer 30 must also be large enough that the illuminating beam 34 is wide enough to illuminate the highest part of the crack 12.

While the embodiment herein refers to determination of crack depth in walls of stainless steel pipe, it is to be understood that the method described applies to the testing of other solid materials for crack or defect depths.

The first step of a preferred method involves placing the transmitting transducer assembly on the outside surface 18 of the pipe 14 being tested near the location of the crack 12. The transducer assemblies can be placed on the pipe 14 manually, or mounted in the portable transducer assembly 26 which is illustrated in FIG. 5. The transducers or the portable transducer assembly 26 may be manually held to the pipe 14, or held in place by a circumferential fastening means. The transmitting transducer assembly 29 is positioned so that the transmitting transducer 30 will generate a shear wave beam 34 at a transmit angle of approximately 45° with respect to the crack 12. The transmit angle of 45° is used since it exceeds the critical angle of the longitudinal wave, with no "clutter" or noise resulting from reflected longitudinal waves. However, for some applications the use of longitudinal waves is contemplated.

The second step in this method is to operate the transmitting transducer 30 in the pulse-echo mode, illuminating the crack 12 and to adjust its position slightly until the reflected signal is maximized, which positively identifies the crack location 12.

The third step is to then switch the transmitting transducer 30 to the transmit mode, and send out repeated pulses to illuminate the crack 12. The receiving transducer assembly 39 is moved along the outside surface 18 of the pipe 14 with respect to the transmitting transducer 30. This is accomplished by moving it manually or by turning the drive screw 62 if the portable transducer assembly 26 is being used. The distance between the two transducer assemblies is adjusted until the signal reflected from the crack 12 received by the receiving transducer 40 (displayed on the oscilloscope 74) is maximized. The position of both transducers is then slightly adjusted to obtain the highest maximum return signal. Once the highest maximum return signal is obtained, the distance between the transducers is then manually or automatically measured or read off the micrometer 64 if the portable transducer assembly 26 is used and the distance is recorded.

In order to insure that the entire length of the crack 12 is illuminated by the transmitted shear wave 34, the transducers should be moved to a number of points around the circumference of the pipe 14, with the three steps described above being repeated at each position. The transducer position should not be moved circumferentially around the pipe more than the width of the ultrasonic illuminating beam 34. The point where the maximum amplitude of the reflected signal is obtained will be the point at which the ultrasonic illuminating beam 34 is illuminating the deepest penetration of the crack 12.

The distance between the two transducers at the point of highest maximum reflected signal is then plotted against calibration curve 84 which is illustrated in FIG. 4. The curve is a graph produced by plotting distance between transducers on the X-axis and crack depth on the Y-axis.

The calibration curve 84 is obtained by performing the above described method on calibration samples or specimens 80 of the same material and wall thickness as the pipe 14 being tested. The calibration samples 80 contain actual cracks or artificially produced cracks 82 of varying known depths. Once the procedure has been accomplished on each known crack 82 the calibration curve 84 can be constructed.

My invention is a significant advancement in the ability of determining the height of cracks or other defects in solid materials. In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. In a method for ultrasonic inspection of solid material of predetermined configuration to determine the depth of a crack therein,
   placing a first ultrasonic transducer acoustically coupled with a surface of the solid material;
   placing a second ultrasonic transducer in acoustical coupling with the surface of the solid material spaced from the first ultrasonic transducer;
   generating an ultrasonic pulse of a selected frequency into the solid material from one of the ultrasonic transducers to acoustically illuminate the crack and produce an acoustical wave form reflected from the crack;
   receiving the reflected acoustical wave form at the other ultrasonic transducer and generating an electrical signal, the magnitude of which corresponds to the magnitude of the reflected acoustical wave form;
   moving at least one of the ultrasonic transducers relative to the other ultrasonic transducer and relative to the crack to vary the magnitude of the electrical signal; and
   determining the distance between the ultrasonic transducers wherein the magnitude of the electrical signal is at a maximum.

2. In the method of claim 1 wherein the ultrasonic pulse generated in solid material is composed of predominately acoustical shear waves.

3. In the method of claim 2 wherein the one acoustical transducer is acoustically coupled to the surface at an angle sufficient to generate a predominance of acoustical shear waves illuminating the crack.

4. In the method of claim 1 wherein the distance between the transducers at the maximum magnitude of the electrical signal is correlated with previously obtained spacing data obtained from calibrated specimens to determine the depth of the crack.

5. In a method for ultrasonically testing a steel pipe adjacent a joint weld to determine the unknown depth of a crack adjacent the weld,
   illuminating the crack with a beam of ultrasonic radiation from a first transducer acoustically coupled to the pipe to generate acoutical wave energy reflected from the crack;
   receiving the reflected ultrasonic wave energy with a second transducer acoustically coupled to the pipe spaced from the first transducer to generate an electrical signal, the magnitude of which corrsponds to the magnitude of the received acoustical wave energy;
   moving the transducers relative to each other to vary the magnitude of the electrical signal;
   measuring the distance between the transducers in which the magnitude of the electrical signal is maximum;
   correlating the measured distance with respect to previously obtained distance data obtained by calibrated specimens of steel pipe having cracks of known depths to determine the depth of the unknown crack.

6. In the method as defined in claim 5 wherein the crack is illuminated with shear wave ultrasonic radiation generated from the first transducer in which the first transducer is acoustically coupled at a selected angle to the steel pipe to generate a predominantly shear wave acoustical beam directed at the crack.

7. In the method as defined in claim 6 wherein the second transducer is acoustically coupled to the steel pipe at a selected angle to receive the reflected acoustical wave energy.

8. In an apparatus for ultrasonically testing a solid material to determine the unknown depth of a crack in the solid material;
   an acoustical coupling frame;
   a first acoustical transducer mounted on the coupling frame for generating an ultrasonic transmit beam;
   a second acoustical transducer mounted on the coupling frames spaced from the first transducer for receiving reflected ultrasonic wave energy and in response thereto generating an electrical signal, the magnitude of which corresponds to the magnitude of the received ultrasonic wave energy;
   first coupling means for acoustically coupling the first transducer to the solid material to illuminate the crack with the transmit ultrasonic beam to generate the reflected ultrasonic wave energy from the crack;
   a second coupling means for acoustically coupling the second transducer to the solid material to receive the reflected ultrasonic wave energy;
   means on the frame for moving the transducers relative to each other to vary the magnitude of the electrical signal;
   means on the frame for determining the distance between the transducers when the magnitude of the electrical signal is maximum.

9. An ultrasonic testing method for determining the unknown depth of a crack in a test pipe section of a predetermined material and wall thickness, comprising the steps of:
   selecting a plurality of calibration pipe sections of the predetermined material and wall thickness having varying known crack depths;
   placing a pair of ultrasonic transducers on each of the calibration pipe sections and ultrasonically illuminating the cracks with one of the transducers and receiving reflected ultrasonic wave energy with the other transducer to generate electrical signals, the magnitude of which vary with the magnitude of the received ultrasonic wave energy;
   adjusting the spacing between the pair of transducers until the magnitudes of the electrical signals are at their maximums;
   correlating the spacing between the pair of transducers with the known depth of the cracks of the calibration pipe sections to obtain a predictable relationship between the depth of the cracks and the spacings between the transducers for the predetermined material and wall thickness;
   placing the pair of ultrasonic transducers on the test pipe section having a crack of unknown depth;
   adjusting the spacing between the pair of transducers until the magnitude of the electric signal is at a maximum;
   correlating the spacing between the pair of transducers with respect to the pipe section having a crack of unknown depth with the relationship of the distance between the transducers and the depth of the cracks from the calibration pipe sections to determine the depth of the crack in the test pipe section.

* * * * *